United States Patent [19]

Chen et al.

[11] 4,101,595
[45] Jul. 18, 1978

[54] CONVERSION OF ETHYL BENZENE TO PARA XYLENE

[75] Inventors: Nai Y. Chen, Titusville, N.J.; William J. Reagan, Yardley, Pa.

[73] Assignee: Mobil Oil Corporation, New York, N.Y.

[21] Appl. No.: 793,017

[22] Filed: May 2, 1977

[51] Int. Cl.² .......... C07C 5/24; C07C 3/62; C07C 7/01
[52] U.S. Cl. .......... 260/668 A; 260/672 T; 260/674 A
[58] Field of Search .......... 260/668 A, 672 T, 674 A

[56] References Cited

U.S. PATENT DOCUMENTS

| | | | |
|---|---|---|---|
| 3,516,925 | 6/1970 | Lawrence et al. | 260/668 A |
| 3,637,881 | 1/1972 | Williams et al. | 260/668 A |
| 3,763,260 | 10/1973 | Pollitzer | 260/668 A |
| 3,766,287 | 10/1973 | Stenmark et al. | 260/668 A |
| 3,767,721 | 10/1973 | Sonoda et al. | 260/668 A |
| 3,856,872 | 12/1974 | Morrison | 260/668 A |
| 3,948,758 | 4/1976 | Bonacci et al. | 260/668 A |
| 3,997,618 | 12/1976 | Cornely et al. | 260/668 A |

*Primary Examiner*—Delbert E. Gantz
*Assistant Examiner*—C. E. Spresser
*Attorney, Agent, or Firm*—Charles A. Huggett; Raymond W. Barclay

[57] ABSTRACT

Monoalkyl benzene having a side chain of at least two carbon atoms is converted to dialkyl benzene having side chains of shorter length than the charge and containing a proportion of para dialkyl benzene in excess of the thermodynamic equilibrium value by reaction over a dual function catalyst comprising a noble metal from Group VIII of the Periodic Table and a crystalline aluminosilicate zeolite of high silica/alumina ratio above 12, a constraint index of 1 to 12, which aluminosilicate is in a state to restrict diffusion of ortho xylene.

18 Claims, 1 Drawing Figure

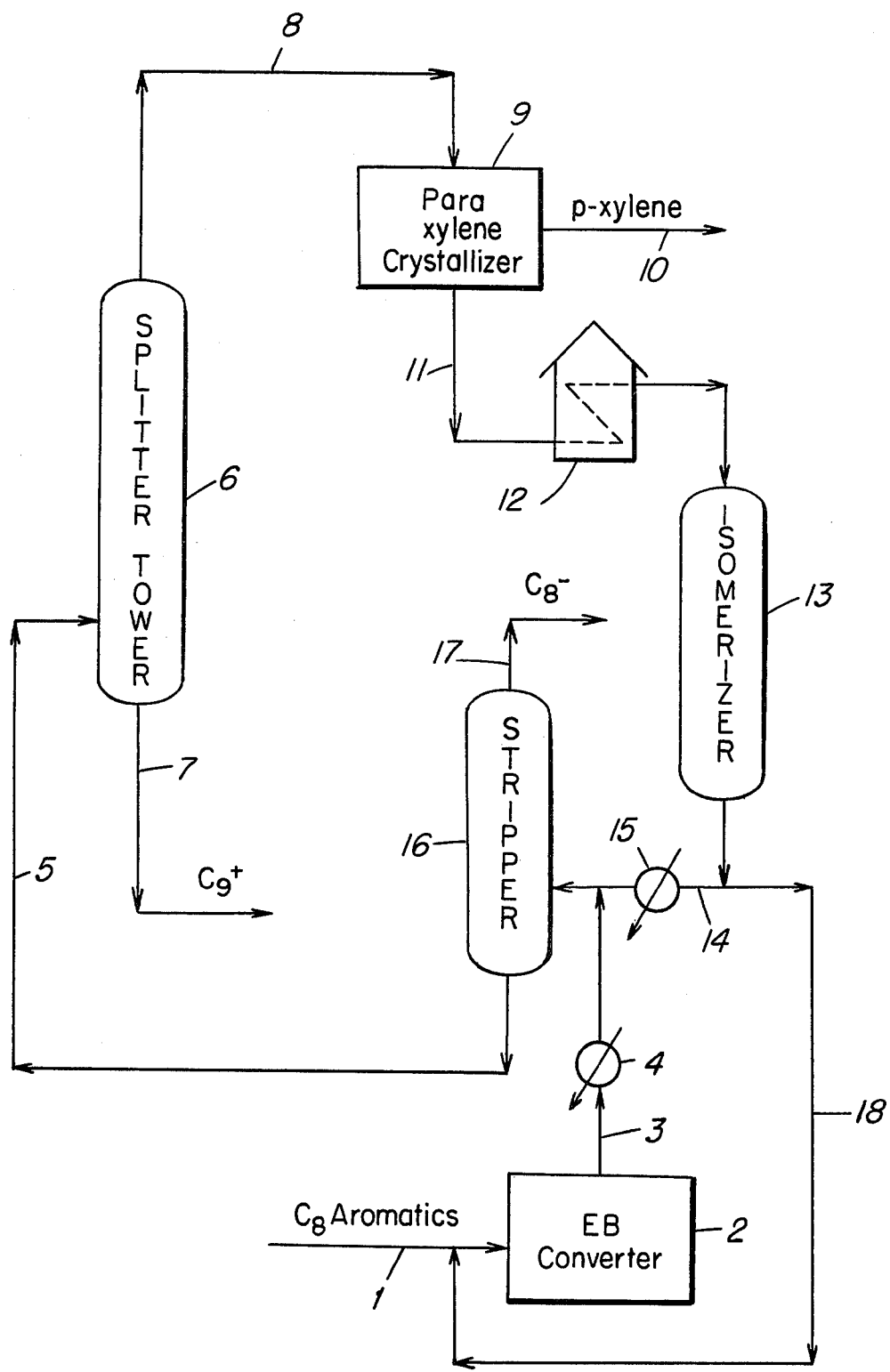

CONVERSION OF ETHYL BENZENE TO PARA XYLENE

FIELD OF THE INVENTION

This invention relates to manufacture of para dialkyl benzenes, typified by para-xylene, and has specific reference to manufacture of the desired product from monoalkyl benzenes having a single side chain of sufficient number of carbon atoms to provide the carbon atoms for desired side chains of the product dialkyl benzene. Thus the invention is exemplified by conversion of ethyl benzene to xylenes at a proportion of para xylene in excess of the thermodynamic equilibrium value. In a preferred embodiment, the invention provides means to process a mixture of $C_8$ aromatics such as that derived from platinum reforming of a petroleum naphtha to a mixture of reduced ethyl benzene content and increased content of paraxylene.

BACKGROUND OF THE INVENTION

Since the announcement of the first commercial installation of Octafining in Japan in June, 1958, this process has been widely installed for the supply of p-xylene. See "Advances in Petroleum Chemistry and Refining" volume 4 page 433 (Interscience Publishers, New York 1961). That demand for p-xylene has increased at remarkable rates, particularly because of the demand for terephthalic acid to be used in the manufacture of polyesters.

Typically, p-xylene is derived from mixtures of $C_8$ aromatics, separated from such raw materials as petroleum naphthas, particularly reformates, usually be selective solvent extraction. The $C_8$ aromatics in such mixtures and their properties are:

|  | Freezing Point° F. | Boiling Point° F. | Density Lbs./U.S. Gal. |
|---|---|---|---|
| Ethyl benzene | −139.0 | 277.1 | 7.26 |
| P-xylene | 55.9 | 281.0 | 7.21 |
| M-xylene | −54.2 | 282.4 | 7.23 |
| O-xylene | −13.3 | 292.0 | 7.37 |

Principal sources are catalytically reformed naphthas and pyrolysis distillates. The $C_8$ aromatic fractions from these sources vary quite widely in composition but will usually be in the range 10 to 32 wt. % ethyl benzene with the balance, xylenes, being divided approximately 50 wt. % meta, and 25 wt. % each of para and ortho.

In turn, calculated thermodynamic equilibra for the $C_8$ aromatic isomers at Octafining conditions are:

| Temperature | 850° F. |
|---|---|
| Wt.% Ethyl benzene | 8.5 |
| Wt.% para xylene | 22.0 |
| Wt.% meta xylene | 48.0 |
| Wt.% ortho xylene | 21.5 |
| TOTAL | 100.0 |

An increase in temperature of 50° F. will increase the equilibrium concentration of ethyl benzene by about 1 wt. % ortho-xylene is not changed and para and meta xylenes are both decreased by about 0.5 wt. %.

Individual isomer products may be separated from the naturally occurring mixtures by appropriate physical methods. Ethyl benzene may be separated by fractional distillation although this is a costly operation. Ortho xylene may be separated by fractional distillation and is so produced commercially. Para xylene is separated from the mixed isomers by fractional crystallization.

As commercial use of para and ortho xylene has increased there has been interest in isomerizing the other $C_8$ aromatics toward an equilibrium mix and thus increasing yields of the desired xylenes.

Octafining process operates in conjunction with the product xylene or xylenes separation processes. A virgin $C_8$ aromatics mixture is fed to such a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

The isomerizer unit itself is most simply described as a single reactor catalytic reformer. As in reforming, the catalyst contains a small amount of platinum and the reaction is carried out in a hydrogen atmosphere.

| Process Conditions | |
|---|---|
| Reactor Pressure | 175 to 225 PSIG |
| Reactor Inlet Temperature Range | 830–900° F. |
| Heat of Reaction | Nil |
| Liquid Hourly Space Velocity | 0.6 to 1.6 Vol/Vol/Hr. |
| Number of Reactors, Downflow | 1 |
| Catalyst Bed Depth, Feet | 11 to 15 |
| Catalyst Density, Lb/Cu. Ft. | 38 |
| Recycle Circulation, Mols Hydrogen/Mol Hydrocarbon Feed | 7.0 to 14.0 |
| Maximum Catalyst Pressure Drop, PSI | 20 |

It will be seen that the system is adapted to produce maximum quantities of p-xylene from a mixed $C_8$ aromatic feed containing all of the xylene isomers plus ethyl benzene. The key to efficient operation for that purpose is in the isomerizer which takes crystallizer effluent lean in p-xylene and converts the other xylene isomers in part to p-xylene for further recovery at the crystallizer.

Among the xylene isomerization processes available in the art, Octafining has been unique in its ability to convert ethyl benzene. Other xylene isomerization processes have required extremely expensive fractionation to separate that component of $C_8$ aromatic fractions. As will be seen from the table of properties above, the boiling point of ethyl benzene is very close to those of p- and m-xylene. Complete removal of ethyl benzene from the charge is impractical. The usual expedient for coping with the problem is an ethyl benzene separation column in the isomerizer-separator loop when using catalyst other than those characteristic of Octafining. It will be seen that Octafining does not have this expensive auxiliary to prevent build up of ethyl benzene in the loop. This advantageous feature is possible because the Octafining catalyst converts ethyl benzene.

The Octafining process has been extensively discussed in the literature, for example:

1. Pitts, P. M., Connor, J. E., Leun, L. N., Ind. Eng. Chem., 47, 770 (1955).

2. Fowle, M. J., Bent, R. D., Milner, B. E., presented at the Fourth World Petroleum Congress, Rome, Italy, June 1955.

3. Ciapetta, F. G., U.S. Pat. No. 2,550,531 (1951).

4. Ciapetta, F. G., and Buck, W. H., U.S. Pat. No. 2,589,189.

5. Octafining Process, Process Issue, Petroleum Refinery, 1st Vol. 38 (1959), No. 11, Nov., p. 278.

A typical charge to the isomerizing reactor (effluent of the crystallizer) may contain 17 wt. % ethyl benzene, 65 wt. % m-xylene, 11 wt. % p-xylene and 7 wt. % o-xylene. The thermodynamic equilibrium varies slightly with temperature. The objective in the isomerization reactor is to bring the charge as near to theoretical equilibrium concentrations as may be feasible consistent with reaction times which do not give extensive cracking and disproportionation.

Ethyl benzene reacts through ethyl cyclohexane to dimethyl cyclohexanes which in turn equilibrate to xylenes. Competing reactions are disproportionation of ethyl benzene to benzene and diethyl benzene, hydrocracking of ethyl benzene to ethylene and benzene and hydrocracking of the alkyl cyclohexanes.

The rate of ethyl benzene approach to equilibrium concentration in a $C_8$ aromatic mixture is related to effective contact time. Hydrogen partial pressure has a very significant effect on ethyl benzene approach to equilibrium. Temperature change within the range of Octafining conditions (830° to 900° F.) has but a very small effect on ethyl benzene approach to equilibrium.

Concurrent loss of ethyl benzene to other molecular weight products relates to % approach to equilibrium. Products formed from ethyl benzene include $C_6+$ naphthenes, benzene from cracking, benzene and $C_{10}$ aromatics from disproportionation and total loss to other than $C_8$ molecular weight. $C_5$ and lighter hydrocarbon by-products are also formed.

The three xylenes isomerize much more selectively than does ethyl benzene, but they do exhibit different rates of isomerization and hence, with different feed composition situations the rates of approach to equilibrium vary considerably.

Loss of xylenes to other molecular weight products varies with contact time. By-products include naphthenes, toluene, $C_9$ aromatics and $C_5$ and lighter hydrocracking products.

Ethyl benzene has been found responsible for a relatively rapid decline in catalyst activity and this effect is proportional to its concentration in a $C_8$ aromatic feed mixture. It has been possible then to relate catalyst stability (or loss in activity) to feed composition (ethyl benzene content and hydrogen recycle ratio) so that for any $C_8$ aromatic feed, desired xylene products can be made with a selected suitably long catalyst use cycle.

A recent development in this art involves the use of a unique class of zeolite catalysts for isomerization of xylenes in a p-xylene recovery loop. The zeolite catalysts designated ZSM-5, ZSM-12 and ZSM-21 as well as other zeolites having like properties will induce extensive disproportionation of ethyl benzene at very low loss of xylene by that reaction, all as described in U.S. Pat. No. 3,856,872, Morrison, dated Dec. 24, 1974. As shown in that patent, isomerization of $C_8$ aromatics with such zeolite catalysts avoids build-up of ethyl benzene in the loop by converting that compound to lower boiling benzene and higher boiling polyalkyl benzenes which are separated by inexpensive splitters and strippers in the loop.

Another solution to the ethyl benzene problem, in addition to Octafining and the Morrison process, has been to supply xylenes which are free of ethyl benzene. The favored sources of such pure xylene streams are techniques for conversion of toluene as by disproportion and methylation.

Disproportion of toluene can be accomplished with porous acid solid catalysts to yield benzene and a mixture of xylenes. The product is, of course, free of ethyl benzene. See, for example, U.S. Pat. No. 3,578,723, Bowes and Wise, dated May 11, 1971.

Reaction of toluene with a methylating agent such as methanol produces xylenes and higher boiling polymethyl benzenes which are readily separated from the product xylenes and may be reacted with toluene to form additional xylenes by transalkylation reactions. Recent developments in synthesis of xylenes by methylation of toluene have been constituted by provision of catalysts which favor production of p-xylene such that the product xylene streams contains a proportion of p-xylene much in excess of the thermodynamic equilibrium value, thereby facilitating separation of p-xylene at reduced cost. These catalysts having enhanced capability for formation of p-xylene generally manifest a restriction on rate of diffusion of xylenes other than the para isomer, a property conveniently measured as rate of diffusion of o-xylene as set out more fully hereinafter.

Because the characteristic that makes these zeolites selective for p-xylene in methylation of toluene is utilized in the present invention, certain of the patents describing methods for preparation and use of such catalysts are herewith incorporated by this reference as disclosure of methods for preparation of catalysts used in this invention:

| | | |
|---|---|---|
| 3,965,207 | Weinstein | June 22, 1976 |
| 3,965,208 | Butter & Kaeding | June 22, 1976 |
| 3,965,209 | Butter & Young | June 22, 1976 |
| 3,965,210 | Chu | June 22, 1976 |
| All in U.S. Classification 260/671 M | | |

SUMMARY OF THE INVENTION

In accordance with a preferred embodiment of the invention, a mixture of eight carbon atom aromatic compounds including substantial amounts of ethyl benzene and each of the three xylene isomers is converted to a product stream of increased xylene content and decreased ethyl benzene content (approaching nil EB) as compared with the charge. This is accomplished without excessive destruction of product by hydrocracking through the use of a catalyst of unique characteristics including low acid activity. The catalyst is preferably selective to formation of para isomers resulting in a product richer in that isomer than predicted by thermodynamic equilibrium data.

The catalyst is of the dual functional type which induces separate reactions by two separate catalysts used together such that product of reaction on one type of catalyst site is then transported to and reacts on a catalyst site of the second type. In contrast with classical dual functional catalyst systems, the catalyst of the present invention manifests shape selective characteristics only with respect to the acid catalyzed step. A metal hydrogenation/dehydrogenation function is nonselective. To achieve the results of the invention the acid function is preferably of reduced activity either by pretreatment of the catalyst or by co-feed of an agent which impairs the acid function, e.g. ammonia, an amine, or other ammonia derived compound. In its preferred aspects, the catalyst is combination of a strong hydrogenation/dehydrogenation metal and a relatively weak acid catalyst derived from the zeolite class specified below.

It will be apparent that the invention is applicable to conversion of ethyl benzene or other mono alkyl benzene alone. Thus pure ethyl benzene can be converted to mixed xylenes, or n-propyl benzene may be converted to methyl ethyl benzenes and the like. Present price structures do not make such conversions of pure monoalkyl benzenes attractive, but the conversions are available by reason of this invention when and if relative prices make that course desirable.

BRIEF DESCRIPTION OF DRAWING

The single FIGURE of the drawing is a diagrammatic flow sheet of an embodiment for practice of the invention wherein the novel reaction is employed to prepare an eight carbon atom aromatics fraction derived from platinum reforming of petroleum naphtha as feed to a conventional loop for recovery of p-xylene by fractional crystallization with isomerization of the rejected o- and m-xylene to yield additional p-xylene for recycle to the crystallizer.

DISCUSSION OF PREFERRED EMBODIMENTS

The process of the invention is adapted to produce para dialkyl benzenes from monoalkyl benzenes of eight to ten carbon atoms, i.e. having a single alkyl side chain of two to four carbon atoms. Preferably the alkyl substituent is normal alkyl, it being found that branched side chains are more subject to hydrocracking than are straight side chains. The feed may be constituted by such monoalkyl benzenes or may be a mixture of mono alkyl benzenes with other substituted aromatics as in the preferred embodiment for conversion of a $C_8$ aromatic fraction containing ethyl benzene and the three xylene isomers.

The charge hydrocarbons are admixed with hydrogen in a molar proportion of about 0.1 to about 15 mols of hydrogen per mol of hydrocarbons and contacted with the dual functional catalyst at 650° – 1000° F. and pressure of 50 to 500 pounds per square inch (psig). Space velocity can vary with severity of other conditions and will generally be about 1.0 to 100 volumes of hydrocarbon per volume of zeolite in the catalyst per hour (LHSV).

The catalyst is a combination of a noble metal of Group VIII of the Periodic Table with a crystalline aluminosilicate zeolite having a silica/alumina ratio of at least 12, a constraint index between 1 and 12 and a crystal density of not less than 1.6 grams per cubic centimeter. In its preferred aspects, the invention contemplates a zeolite of reduced acid function to minimize losses to hydrocracking. One way to achieve this result is to add to the charge a catalyst poison for acid catalyst such as an amine. Alternatively, the zeolite may be reduced in activity by steaming, partial exchange with such cations as alkali metals, partial coking and like known deactivating techniques. When operating without a catalyst poison in the charge, the zeolite should be deactivated to a reduced activity, conveniently measured as alpha value, between 0.05 and 1. The zeolite should also show restricted diffusion of xylenes other than p-xylene, a property related to selectivity for production of p-xylene. The zeolites employed in practice of preferred embodiments of the invention will have an o-xylene sorption time greater than 10 minutes for 30 percent of the total capacity of the zeolite for sorbed xylene at equilibrium under conditions of the test presently to be described.

The alpha value reflects the relative activity of the catalyst with respect to a high activity silica-alumina cracking catalyst. To determine the alpha value as such term is used herein, n-hexane conversion is determined at about 1000° F. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 1000° F. Catalytic activity of the catalysts are expressed as multiple of this standard, i.e. the silica-alumina standard. The silica-alumina reference catalyst contains about 10 weight percent $Al_2O_3$ and remainder $SiO_2$. This method of determining alpha, modified as described above, is more fully described in the Journal of Catalysts, Vol VI, Pages 278–287, 1966.

The measurements of hydrocarbon sorption capacities and rates are conveniently carried out gravimetrically in a thermal balance. In particular, it has been found that an equilibrium sorption capacity of xylene, which can be either para, meta, ortho or a mixture thereof, preferably para-xylene since this isomer reaches equilibrium within the shortest time of at least 1 gram per 100 grams of zeolite measured at 120° C and a xylene pressure of 4.5 ± 0.8 mm of mercury and an orthoxylene sorption time for 30 percent of said capacity of greater than 10 minutes (at the same conditions of temperatures and pressure) are required in order to achieve the desired selective production of para dialkyl substituted benzenes.

It has been found that zeolites exhibiting very high selectivity for para-dialkylbenzene production require a very long time up to and exceeding a thousand minutes to sorp o-xylene in an amount of 30% of total xylene sorption capacity. For those materials it is more convenient to determine the sorption time for a lower extent of sorption, such as 5%, 10% or 20% of capacity, and to estimate the 30% sorption time by applying the following multiplication factors F as illustrated for 5% sorption:

$$t_{0.3} = F \cdot t_{0.05}$$

| Percent of sorption capacity | Factor (F) to Estimate 30% Sorption Time |
|---|---|
| 5 | 36 |
| 10 | 9 |
| 20 | 2.2 |

Particularly preferred are those zeolites having a silica to alumina ratio of at least about 12 and a constraint index within the approximate range of 1 to 12. These zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° F and 950° F to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specificed zeolites but that such are the cumlative result of several variables used in determination and calculation thereof. Thus, for a given zeolite depending on the temperature employed within the aforenoted range of 550° F to 950° F, with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variable extremes. However, in all instances, at a temperature within the above-specified range of 550° F to 950° F, the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. Application Ser. No. 528,060, filed November 29, 1974. This zeolite can be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)R_2O : (0-0.6)M_2O : Al_2O_3 : xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium, an x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33Å.

TABLE I

| d (Å) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

|  | Broad | Preferred |
|---|---|---|
| $R^+/(R^+ + M^+)$ | 0.2–1.0 | 0.3–0.9 |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

$$(0.3-2.5)R_2O : (0-0.8)M_2O : Al_2O_3: > 8\ SiO_2$$

wherein R is an organic nitrogen-containing cation derived from ethylenediamine or pyrrolidine and M is an alkali metal cation, and is characterized by a specified X-ray powder diffraction pattern.

In a preferred synthesized form the zeolite has a formula, in terms of mole ratios of oxides and in the anhydrous state, as follows:

$$(0.4-2.5)R_2O : (0.0.6)M_2O : Al_2O_3 : xSiO_2$$

wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33Å. Close examination of some individual samples of ZSM-35 may show a very weak line at 11.3–11.5Å. This very weak line, however, is determined not to be a significant line for ZSM-35.

TABLE II

| d (Å) | I/Io |
|---|---|
| 9.6 ± 0.20 | Very Strong- |

TABLE II-continued

| d (Å) | I/Io |
|---|---|
| | Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas the ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| | Broad | Preferred |
|---|---|---|
| $R^+/(R^+ + M^+)$ | 0.2–1.0 | 0.3–0.9 |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 | wherein R is an organic nitrogen-containing cation derived from pyrrolidine or ethylenediamine an M is an alkali metal ion, an maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. THe solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possible because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicate are ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | | Framework Density | |
|---|---|---|---|---|
| Ferrierite | 0.28 | cc/cc | 1.76 | g/cc |
| Mordenite | .28 | | 1.7 | |
| ZSM-5, -11 | .29 | | 1.79 | |
| Dachiardite | .32 | | 1.72 | |
| L | .32 | | 1.61 | |
| Clinoptilolite | .34 | | 1.71 | |
| Laumontite | .34 | | 1.77 | |
| ZSM-4 (Omega) | .38 | | 1.65 | |
| Heulandite | .39 | | 1.69 | |

-continued

| Zeolite | Void Volume | Framework Density |
| --- | --- | --- |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel copper, zinc, palladium, calcium or rare earths metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mine or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

In a preferred embodiment, the crystalline aluminosilicate zeolites employed may have undergone modification prior to use by selective precoking thereof to deposit at least about 1 weight percent and generally between about 2 and about 40 weight percent of coke thereon, based on the weight of total catalyst. If zeolite is employed in substantially pure form or in combination with a low coking binder, such as silica, then the weight percent of coke is generally in the range of 2 to 10 weight percent. When the zeolite is combined with a binder of high coking tendencies, such as alumina coke constant of the total catalyst is in the approximate range of 10 to 40 weight percent. Precoking can be accomplished by contacting the catalyst with a hydrocarbon charge, e.g. toluene, under high severity conditions or alternatively at a reduced hydrogen to hydrocarbon concentration, i.e. 0 to 1 mole ratio of hydrogen to hydrocarbon for a sufficient time to deposit the desired amount of coke thereon. Prior modification of the zeolite may also be suitably effected by combining therewith a small amount, generally in the range of about 2 to about 30 weight percent, of a difficulty reducible oxide, such as oxides of antimony, phosphorus, boron or magnesium. Combination of the desired oxide with the zeolite can readily be effected by contacting the zeolite with a solution of an appropriate compound of the element to be introduced, followed by drying and calcining to convert the compound to its oxide form.

The above objects are attained in a process illustrated in the single FIGURE of drawings which is a diagrammatic representation of apparatus suited to practice of the invention.

A mixture of $C_8$ aromatics is supplied to the system by line 1, as from solvent extraction of a narrow cut taken by distillation of product of reforming a petroleum naphtha over platinum on alumina catalyst in the presence of hydrogen. The feed, constituted by an approximately equilibrium mixture of ethyl benzene and the three xylene isomers is passed to ethyl benzene converter 2 in which the ethyl benzene is converted in large measure to xylenes, including a proportion of p-xylene in excess of the equilibrium value in accordance with the process of this invention. Conversion products, including $C_8$ naphthenes, aliphatic hydrocarbons of lower boiling point, as well as the xylenes present in the feed, xylenes formed by conversion of ethyl benzene and unconverted ethyl benzene pass by line 3 and cooler 4 for introduction to the conventional recovery/isomerization loop.

A blended stream of fresh feed from converter 2 and recycle xylenes is stripped of components boiling below the range of eight carbon atom aromatics in a manner presently to be described and admitted to splitter tower 6 from which a heavy end is withdrawn by line 7. In the embodiment shown, that heavy end is constituted by $C_930$ aromatics derived from disproportion of ethyl benzene and from the minor side reaction of transalkylation of xylenes in the isomerizer as well as heavier components resulting from reaction in converter 2. Alternatively, when it is desired to recover o-xylene a a separate product, splitter tower 6 may be operated to include o-xylene in the bottoms which are then passed to distillation for separation of o-xylene from $C_9+$ aromatic (not shown).

The overhead of splitter tower 6 passes by line 8 to means for separation of p-xylene. In the embodiment illustrated, p-xylene is separated by fractional crystallization in crystallizer 9, involving chilling and filtration of p-xylene crystals from the liquid phase, for example, in the manner described by Machell et al. U.S. Pat. No. 3,622,013, dated May 9, 1972. It will be understood that other systems for p-xylene separation may be used in a plant for practice of this invention, e.g. selective sorption as described in Cattanach U.S. Pat. No. 3,699,182 dated Oct. 17, 1972. By whatever means separated, high purity p-xylene is withdrawn as product by line 10.

The stream of $C_8$ aromatics of reduced p-xylene content is withdrawn from crystallizer 9 by line 11, passed through heater 12 and admitted to catalytic isomerizer 13 where it is contacted at reaction condition with a suitable catalyst for isomerization of xylenes. The principal reaction in isomerizer 13 is shifting of methyl groups in xylene molecules as toward the equilibrium concentrations of the three xylenes. According to this invention, isomerizer 13 is operated at relatively mild conditions as compared with prior art practices in which one function of the isomerizer is to convert ethyl benzene, as by disproportionation to benzene and diethyl benzene. Conditions to accomplish that purpose also induce some conversion of xylenes by like reactions. Isomerizer 13 is preferably operated at conditions to cause little or substantially no conversion of ethyl benzene.

A slip stream constituting a minor proportion of effluent from isomerizer 13 is diverted intermittently or continuously by line 18 to the charge line 1 for ethyl benzene converter 2. The balance of isomerizate produced in isomerizer 13 is mixed with the product in line 3 from converter 2 and is transferred by line 14 through heat exchanger 15 to stripper 16. The light ends of the mixture (benzene, toluene and normally gaseous hydrocarbons) are taken overhead by line 17 from stripper 16 and the balance passes by line 5 to be blended with fresh feed an recycled in the process.

The inherently high activity of zeolites utilized in this invention is severly reduced for the present purpose. This result may be achieved by treating the zeolite itself to reduce its activity as measured by the alpha test or a catalyst poison may be introduced with the charge to converter 2 for equivalent results. In addition, the zeolite will exhibit restricted diffusion of o-xylene as discussed. The restricted diffusion effect can be achieved by utilizing large crystals of, e.g. zeolite ZSM-5, having average dimension of individual crystals about 0.5 microns and greater. Alternatively, small crystal zeolites may be modified to show the restricted diffusion effect by techniques known to the art, for example those shown in patents cited supra.

Comparative runs reported hereinafter utilize a large crystal zeolite ZSM-5 having a silica/alumina mol ratio of 70 and an average crystal dimension of 2 microns. The desired reduction in activity was accomplished by addition of propylamine with the charge. Such comparisons avoid some possibilities of the results being obscured by changes in the catalyst, charge or other parameters from one run to another. The results here reported are preliminary and indicate significant prospect for improvement by variation from conditions here reported. These results do establish the feasibility of the conversion of ethyl benzene and other monoalkyl aromatics with these catalysts despite the fact that excessive side reactions in some cases result in yields which appear economically unattractive at the conditions actually used.

EXAMPLES

Exemplary runs were conducted with catalysts derived from ZSM-5 of 2 micron average crystal size and silica/alumina mol ratio of 70. The zeolite was converted to the acid form (HZSM-5) by conventional techniques of base exchange with ammonium ion and calcining. That zeolite was combined with a metal function by various modes. In some instances, the zeolite was composited with a conventional reforming catalyst of 0.35 weight percent platinum and 0.35 weight percent rhenium on gamma alumina to provide metal function. For some runs, metal function was provided by base exchange of the zeolite with cobalt nitrate or platinum amine solution. Still other catalysts were prepared by impregnating HZSM-5 with chlorplatinic acid and calcining. The specific catalysts employed, reaction conditions and results obtained are all shown in Table III reporting several conversions in which the charge was ethyl benzene.

TABLE III

Ethylbenzene, Conversion Studies
800° F., 500 psig, $H_2$/Hydrocarbon = 10/1 molar
Effect of Metal & n-propyl amine

| Run No. | 1 | 2 | 3 | 4 |
|---|---|---|---|---|
| Catalyst Description | 50%Pt,Re/Al$_2$O$_3$ 50%BX CoZSM-5 | 90%Pt,Re/Al$_2$O$_3$ 10%BX CoZSM-5 | 90%Pt,Re/Al$_2$O$_3$ 10%BX CoZSM-5 | 100% BX Co ZSM-5 |
| LHSV on Zeolite | 30 | 32 | 32 | 32 |
| Amine, Vol.% | 0 | 0 | 5 | 0 |
| EB Remaining % | 2.3 | 5.0 | 37.7 | 27.5 |
| C$_8$ Naphthenes | 0.9 | 6.8 | 47.5 | 0.4 |
| % Conversion | 96.8 | 88.2 | 14.8 | 72.1 |
| Conversion Products wt.% | | | | |
| C$_5^-$ | 45.8 | 55.2 | 18.9 | 24.7 |
| C$_6$ | 0.2 | 22.8 | 10.5 | 1.8 |
| Benzene | 47.6 | 4.0 | 3.4 | 59.6 |
| Toluene | 3.5 | 1.1 | 6.1 | 8.3 |
| Xylenes | 0.9 | 14.2 | 45.9 | 1.4 |
| C$_9$+ Aromatics | 1.0 | 0.4 | 0.7 | 1.9 |
| Other | 1.0 | 2.3 | 14.5 | 2.2 |
| Total Product | 100.0 | 100.0 | 100.0 | 99.9 |
| % para in xylenes | — | 25.6 | 80.5 | 30.0 |
| Run No. | 5 | 6 | 7 | 8 |
| Catalyst Description | 86%Pt,Re/Al$_2$O$_3$ 14% HZSM-5 | 86%Pt,Re/Al$_2$O$_3$ 14% HZSM-5 | 100% BX Pt ZSM-5 | 100% BX Pt ZSM-5 |
| LHSV on Zeolite | 25 | 25 | 17.4 | 11.2 |
| Amine, Vol.% | 0 | 1 | 0 | 1 |
| EB Remaining % | 4.5 | 37.7 | 1.8 | 33.0 |
| C$_8$ Naphthenes | 6.3 | 35.6 | 0.3 | 13.4 |
| % Conversion | 89.2 | 26.7 | 97.9 | 53.6 |
| Conversion Products wt.% | | | | |
| C$_5^-$ | 55.9 | 27.3 | 75.4 | 51.5 |
| C$_6$ | 20.5 | 9.0 | 11.3 | 12.5 |
| Benzene | 4.4 | 3.4 | 10.5 | 6.3 |

TABLE III-continued

Ethylbenzene, Conversion Studies
800° F., 500 psig, H$_2$/Hydrocarbon = 10/1 molar
Effect of Metal & n-propyl amine

|  |  |  |  |  |  |
|---|---|---|---|---|---|
| Toluene | 1.2 | 5.2 | 0.7 | 1.3 |  |
| Xylenes | 13.6 | 41.6 | 1.7 | 22.4 |  |
| C$_9$+ Aromatics | 1.0 | 2.6 | 0.2 | 0.9 |  |
| Other | 3.4 | 10.9 | 0.1 | 5.1 |  |
| Total Product | 100.0 | 100.0 | 99.9 | 100.0 |  |
| % para in xylenes | 23.7 | 74.4 | 23.5 | 38.3 |  |
| Run No. | 9 | 10 | 11 | 12 | 13 |
| Catalyst Description | 100% BX Pt ZSM-5 | 100% BX Pt ZSM-5 | 100% (Imp) Pt ZSM-5 | Steamed 100% (Imp) Pt ZSM-5 | Steamed 100% (Imp) Pt ZSM-5 |
| LHSV on Zeolite | 7.2 | 14.6 | 14.0 | 16.0 | 14.0 |
| Amine, Vol.% | 2 | 5 | 0 | 1 | 2 |
| EB Remaining % | 21.8 | 43.3 | 24.0 | 36.5 | 40.6 |
| C$_8$ Naphthenes | 17.5 | 25.3 | 20.1 | 33.3 | 37.2 |
| % Conversion | 60.7 | 31.4 | 55.9 | 30.2 | 22.2 |
| Conversion Products wt.% |  |  |  |  |  |
| C$_5$$^-$ | 50.2 | 33.1 | 51.9 | 27.1 | 19.4 |
| C$_6$ | 8.4 | 6.0 | 11.8 | 5.6 | 4.5 |
| Benzene | 2.1 | 2.8 | 3.2 | 2.3 | 1.7 |
| Toluene | 1.6 | 3.8 | 0.5 | 5.4 | 0.9 |
| Xylenes | 28.5 | 41.4 | 24.5 | 46.4 | 52.3 |
| C$_9$+ Aromatics | 0.6 | 0.3 | 0.5 | 0.3 | 2.7 |
| Other | 8.6 | 12.4 | 7.5 | 12.9 | 18.9 |
| Total Product | 100.0 | 99.8 | 99.9 | 100.0 | 100.4 |
| % para in xylenes | 36.4 | 66.2 | 40.1 | 63.6 | 67.7 |

Notes to Table III: eight carbon atom naphthenes are involved in a reversible reaction with ethyl benzene and are treated as unconverted charge. Conversion product "other" includes seven and eight carbon atom paraffins. The notation "BX" indicates metal introduced by base exchange; "Imp" denotes impregnated metal.

A dual-functional mechanism for the conversion of ethylbenzene is reasonably well established. The proposed mechanism is similar to the explanation for the aromatization of methylcyclopentane in reforming. The first step involves the formation of a reactive intermediate by partial hydrogenation of ethylbenzene on a metal site. This intermediate then migrates to an acid site where isomerization to alkylcyclopentenes and dimethylcyclohexanes take the place. The reaction sequence is completed when these intermediates migrate to a metal site for conversion to xylenes. In the presence of an active acid catalyst, such as HZSM-5, these reactive intermediates can undergo side reactions such as ring opening, cracking, etc. Since HZSM-5 catalysts are very effective for these reactions, there was no reason to believe that para-xylene could be selectively produced from ethylbenzene.

These predictions were indeed noted in initial experiments for the conversion of ethylbenzene over a catalyst consisting of a 1 to 1 mixture of reforming catalyst and CoZSM-5C. The reaction products contained mainly C$_2$ to C$_6$ paraffins and some benzene. These products were formed by the side reactions of ring opening, cracking and dealkylation. However, when this catalyst was modified to increase the hydrogenation activity and lower the acid activity, xylenes were efficiently produced from ethyl benzene. In addition, the para-xylene selectivities observed are comparable to the values reported for toluene disproportionation over "selectivated" HZSM-5 catalysts.

The key feature of the novel catalyst composition appears to be a strong hydrogenation function coupled with a low acidity, shape selective zeolite component. This optimum combination may be achieved in a number of ways: variations in the ratios of reforming catalyst and zeolite, and control of the acidity of the two components. This acidity control may be achieved by known techniques such as steam treatment, nitrogen poisoning, base exchange or combination of these methods.

The scope of this type of reaction is demonstrated by the conversion of n-propybenzene to significant yields of paraethyl toluene as shown in Table IV.

TABLE IV

| Run No. | 14 |
|---|---|
| Charge | n-propyl benzene |
| Catalyst Description | 86% Pt/Al$_2$O$_3$ 14% HZSM-5 |
| LHSV on zeolite | 45 |
| n-propyl amine vol. % | 5 |
| Pr Benzene remaining % | 69.6 |
| C$_9$ naphthenes | 10.4 |
| % conversion | 20 |
| Conversion products wt.% |  |
| Ethyl toluenes | 15.0 |
| C$_5$$^-$ | 37.5 |
| C$_6$ | 24.0 |
| benzene | 7.5 |
| toluene | 4.0 |
| xylenes | 10.0 |
| other | 2.0 |
| Total | 100.0 |
| % para in ethyl toluenes | ca. 50 |

The experiments reported above were carried out in a pressure microunit with on-line product sampling and GC analysis devices. The reactions were routinely carried out with 1-2 cc of catalyst, reactor pressure of 500 psig, H$_2$/hydrocarbon ratio of 10:1.

Material balance was made on a no loss basis, based on the on-line GC analysis of the reactor effluent. Pure, one component hydrocarbon feeds were used. In some cases, n-propylamine was added to the feed to moderate the acid activity of the catalyst.

The following catalysts were studied:

(1) Cobalt ZSM-5 prepared by ion exchange of large crystal ZSM-5 with Co(NO$_3$)$_2$ solution.

(2) A 50/50 weight ratio physical mixture of Pt-Re/alumina reforming catalyst (0.35% Pt, 0.35% Re on gamma alumina) and CoZSM-5, prepared by ball milling reforming catalyst with CoZSM-5, and the composition then repelleted and sized to 40/60 mesh particles.

(3) A 90/10 weight ratio mixture of reforming catalyst and CoZSM-5.

(4) An 86/14 weight ratio mixture of reforming catalyst and HZSM-5.

(5) a Pt exchanged ZSM-5 was prepared by two successive reflux treatments of $NH_4ZSM-5$ with an aqueous solution of $Pt(NH_3)_4Cl_2$. The platinum content of the aqueous solution was sufficient to yield a catalyst with 1.2 wt. % if 100% exchange occurred. The actual platinum content of the finished catalyst was 0.69 wt. %.

(6) a steamed ZSM-5 sample, (3 hours at 1000° F., 100% steam) was impregnated with 0.5 wt. % Pt. The impregnation solution consisted of chloroplatinic acid dissolved in acetone. The finished catalyst had an alpha value of 90.

Under conditions chosen for this study, ethylbenzene can either undergo selective isomerization or be dealkylated and/or hydrocracked to lower boiling hydrocarbons.

The necessity of decreasing acid activity to avoid loss of $C_8$ hydrocarbons and to achieve high para-selectivity was demonstrated by the experimental results shown in Table III.

Para-xylene selectivity in excess of 60% of all xylenes was obtained with the following catalyst systems:
1. 90/10 reforming catalyst/CoZSM-5 + 5% propylamine in feed
2. 86/14 reforming catalyst/HZSM-5 + 1% propylamine in feed
3. Pt exchanged HZSM-5 + 5% propylamine in feed
4. Pt/steamed ZSM-5 + 1% propylamine in feed However, the conversion of ethylbenzene to $C_7^-$ products was quite substantial in all cases. This suggests that further reduction in acid activity and increase in reaction temperature and/or a decrease in reaction pressure would be desirable to preserve the aromatic rings.

The results shown in Table III can also be used to illustrate a number of points.

(1) In the absence of propylamine, the acidity of the mixed catalyst system was excessive. The results show the predominance of dealkylation, ring opening and hydrocracking reactions. This is further confirmed by the favorable results of reducing the concentration of ZSM-5 in the catalyst mixture.

(2) The cobalt in the CoZSM-5 sample did not function as a hydrogenation/dehydrogenation component as evidenced by the predominance of the dealkylation reaction and the absence of naphthenes.

(3) Although the physical makeup of these catalysts is quite different, the similarity of the results suggest that considerable freedom is available to modify the catalyst composite for optimal xylene selectivity. The data also demonstrate that the catalytic shape selectivity of the metal function is not required to achieve selective production of the para-isomer.

It is believed that the reaction path for p-xylene production differs from the classical dual functional conversion of alkylcyclopentanes to alkyl aromatics in only one aspect, viz., the acid catalyzed skeletal ring isomerization reaction takes place within the channels of ZSM-5, such that para-dimethyl cyclohexenes or para-dimethyl cyclohexanes are formed preferentially to the ortho- or meta-isomers. In addition, the rate of diffusion of the para-isomers is significantly higher than that of the ortho- and meta-isomers. Thus, the reaction can be written as follows:

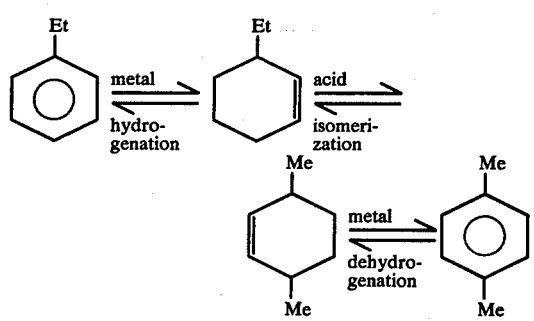

The compounds listed as $C_8$ naphthenes in Table III include ethylcyclohexane and isomers of dimethylcyclohexanes. It is evident that these initial exploratory experiments were made at too low a temperature and/or too high a pressure to favor aromatics formation.

The proposed mechanism for the conversion of ethylbenzene to xylenes would suggest that other alkylbenzenes may undergo similar sketal isomerizations. For this reason, cumene and n-propylbenzene were allowed to react under similar test conditions over several of the catalysts mentioned above. For the cumene case, the excessive acidity of the catalysts (even with 5% propylamine added to charge) resulted in a high level of dealkylation. The n-propylbenzene was less susceptible to dealkylation and representative test results are presented in Table IV.

The overall selectivity for the desired ethyl toluene versus the $C_5^-$ product is quite unfavorable. However, the reality of selective production of greater than equilibrium concentrations of para-ethyl toluene from n-propylbenzene has been demonstrated.

We claim:
1. In a process for recovering para-xylene from a source mixture of eight carbon atom aromatics which contains ethyl benzene and each of the xylene isomers by extracting para xylene from a mixture of xylene isomers, isomerizing the resultant mixture lean in para xylene to convert ortho- or meta-xylene to para-xylene, recycling the resultant isomerizate to the said extraction and adding to the loop of extraction and isomerization fresh charge containing each of the xylene isomers; the improvement whereby to provide said fresh charge reduced in ethyl benzene content and enhanced in para-xylene content above the thermodynamic equilibrium value which comprises converting said source mixture at conversion conditions of temperature between about 650° F. and 1000° F., pressure of 50 to 500 pounds per square inch, in admixture with 0.1 to 15 mols of hydrogen per mol of hydrocarbon and a space velocity of 1 to 100 volumes of hydrocarbon per volume of the hereinafter recited zeolite with a catalyst composite of a strong hydrogenation/dehydrogenation metal of Group VIII of the Periodic Table and a shape selective moderate acid zeolite characterized by a silicate/alumina ratio greater than 12, a constraint index of 1 to 12, a xylene sorption capacity greater than 1 gram per 100 grams of zeolite and an ortho-xylene sorption time for 30 percent of said capacity greater than 10 minutes, said sorption capacity and sorption time being measured at 120° C. and a xylene pressure of 4.5 ± 0.8 mm. of mercury.

2. A process according to claim 1 wherein said zeolite has an alpha value of 0.05 to 1.

3. A process according to claim 1 wherein a substance which impairs acid activity of zeolite catalysts is added to the said source mixture.

4. A process according to claim 3 wherein said substance is an amine.

5. A process according to claim 4 wherein said amine is n-propylamine.

6. A process according to claim 4 wherein said amine is added in an amount equal to 1 to 5% of hydrocarbons in said source mixture.

7. A process for converting a monoalkyl benzene having an alkyl substituent of 2 to 4 carbon atoms to a dialkyl benzene mixture in which para isomer is present in a proportion greater than the thermodynamic equilibrium value which comprises converting said monoalkyl benzene at conversion conditions of temperature between about 650° F. and 1000° F., pressure of 50 to 500 pounds per square inch, in admixture with 0.1 to 15 mols of hydrogen per mol of monoalkyl benzene and a space velocity of 1 to 100 volumes of dialkyl benzene per volume of the hereinafter recited zeolite with a catalyst composite of a strong hydrogenation/dehydrogenation metal of Group VIII of the Periodic Table and a shape selective moderate acid zeolite characterized by a silica/alumina ratio greater than 12, a constraint index of 1 to 12, a xylene sorption capacity greater than 1 gram per 100 grams of zeolite and an ortho-xylene sorption time for 30 percent of said capacity greater than 10 minutes, said sorption capacity and sorption time being measured at 120° C. and a xylene pressure of 4.5 ± 0.8 mm. of mercury.

8. A process according to claim 7 wherein said monoalkyl benzene is ethyl benzene.

9. A process according to claim 7 wherein said monoalkyl benzene is n-propyl benzene.

10. A process according to claim 7 wherein said zeolite has an alpha value of 0.05 to 1.

11. A process according to claim 7 wherein a substance which impairs acid activity of zeolite catalysts is added to the monoalkyl benzene.

12. A process according to claim 11 wherein said substance is an amine.

13. A process according to claim 12 wherein said amine is n-propylamine.

14. A process according to claim 12 wherein said amine is added in an amount equal to 1 to 5% of said monoalkyl benzene.

15. A process according to claim 7 wherein said metal is a noble metal from periods 5 and 6 of Group VIII.

16. A process according to claim 7 wherein said metal is platinum.

17. A process according to claim 1 wherein said metal is a noble metal from periods 5 and 6 of Group VIII.

18. A process according to claim 1 wherein said metal is platinum.

* * * * *

UNITED STATES PATENT AND TRADEMARK OFFICE
CERTIFICATE OF CORRECTION

PATENT NO. : 4,101,595

DATED : July 18, 1978

INVENTOR(S) : Nai Y. Chen and William J. Reagan

It is certified that error appears in the above-identified patent and that said Letters Patent are hereby corrected as shown below:

Column 13, line 40, "mine" should read --mined--.

Column 14, line 44, "$C_9 30$" should read --$C_9+$--.

Column 14, line 48, "a a" should read --as a--.

Column 14, line 52, "aromatic" should read --aromatics--.

Signed and Sealed this

Seventeenth Day of May 1983

[SEAL]

Attest:

DONALD J. QUIGG

Attesting Officer     Acting Commissioner of Patents and Trademarks